United States Patent
Heinsbergen et al.

(10) Patent No.: US 10,420,891 B2
(45) Date of Patent: Sep. 24, 2019

(54) EXPANDING PLUNGER RODS FOR SYRINGES

(71) Applicant: UNL Holdings LLC, New York, NY (US)

(72) Inventors: Daniel A. Heinsbergen, Narberth, PA (US); Bryan Frederick Bell, Jr., Red Lion, PA (US); Robert Scott Russo, Gettysburg, PA (US); Dinesh Panneerselvam, Thorndale, PA (US); Brandon J. McKee, Nesquehoning, PA (US)

(73) Assignee: UNL Holdings LLC, New York, NY (US)

( * ) Notice: Subject to any disclaimer, the term of this patent is extended or adjusted under 35 U.S.C. 154(b) by 268 days.

(21) Appl. No.: 15/116,153

(22) PCT Filed: Feb. 3, 2015

(86) PCT No.: PCT/US2015/014255
§ 371 (c)(1),
(2) Date: Aug. 2, 2016

(87) PCT Pub. No.: WO2015/117131
PCT Pub. Date: Aug. 6, 2015

(65) Prior Publication Data
US 2017/0182254 A1    Jun. 29, 2017

Related U.S. Application Data

(60) Provisional application No. 61/935,081, filed on Feb. 3, 2014.

(51) Int. Cl.
*A61M 5/315* (2006.01)
*A61M 5/28* (2006.01)
*A61M 5/31* (2006.01)

(52) U.S. Cl.
CPC .......... *A61M 5/31511* (2013.01); *A61M 5/28* (2013.01); *A61M 5/3134* (2013.01);
(Continued)

(58) Field of Classification Search
CPC .......... A61M 5/31511; A61M 5/31515; A61M 5/315; A61M 2005/31518; A61M 5/2422;
(Continued)

(56) References Cited

U.S. PATENT DOCUMENTS 1,496,126 A * 6/1924 Livingstone .......... A61M 5/204
222/372
5,858,001 A * 1/1999 Tsals ................. A61M 5/14248
604/135

(Continued)

OTHER PUBLICATIONS

European Patent Office, International Search Report in International Patent Application No. PCT/US2015/014255, dated Apr. 10, 2015, 3 pp.

(Continued)

*Primary Examiner* — Bhisma Mehta
*Assistant Examiner* — Hong-Van N Trinh
(74) *Attorney, Agent, or Firm* — Hamilton, Brook, Smith & Reynolds, P.C.

(57) ABSTRACT

An expanding plunger rod for a syringe is configured to transition from a packaged configuration to an expanded configuration for operation. The rod includes a substantially cylindrical outer sleeve having a closed-off bottom end and an open upper end, and an inner rod having a lower end and an upper end. The inner rod is slidably disposed coaxially within the outer sleeve. In the packaged configuration, the inner rod is nested within the outer sleeve. In the expanded configuration, the inner rod is disposed substantially axially
(Continued)

above the outer sleeve, and the inner rod locks axially in place to prevent transition from the expanded to the packaged configuration.

11 Claims, 8 Drawing Sheets

(52) U.S. Cl.
CPC ...... *A61M 5/3135* (2013.01); *A61M 5/31501* (2013.01); *A61M 5/31515* (2013.01); *A61M 2005/31518* (2013.01)

(58) Field of Classification Search
CPC ...... A61M 5/2429; A61M 2005/31598; A61M 2005/31508; A61M 5/3137; F16B 7/042; F16B 7/0406; F16B 7/0413

See application file for complete search history.

(56) References Cited

U.S. PATENT DOCUMENTS

| | | |
|---|---|---|
| 7,976,510 B2 | 7/2011 | Janish et al. |
| 2009/0318880 A1* | 12/2009 | Janish ................ A61M 5/31511 604/228 |
| 2010/0228200 A1 | 9/2010 | Moed |
| 2011/0196313 A1* | 8/2011 | Mudd ................ A61M 5/31511 604/219 |
| 2012/0277664 A1* | 11/2012 | Macy, Jr. .............. A61M 1/007 604/28 |
| 2013/0085457 A1 | 4/2013 | Schiff et al. |
| 2013/0304021 A1* | 11/2013 | Cabiri ................ A61M 5/31511 604/506 |
| 2015/0217045 A1* | 8/2015 | Bente, IV .......... A61M 5/1454 604/135 |

OTHER PUBLICATIONS

European Patent Office, Written Opinion in International Patent Application No. PCT/US2015/014255, dated Apr. 10, 2015, 6 pp.

* cited by examiner

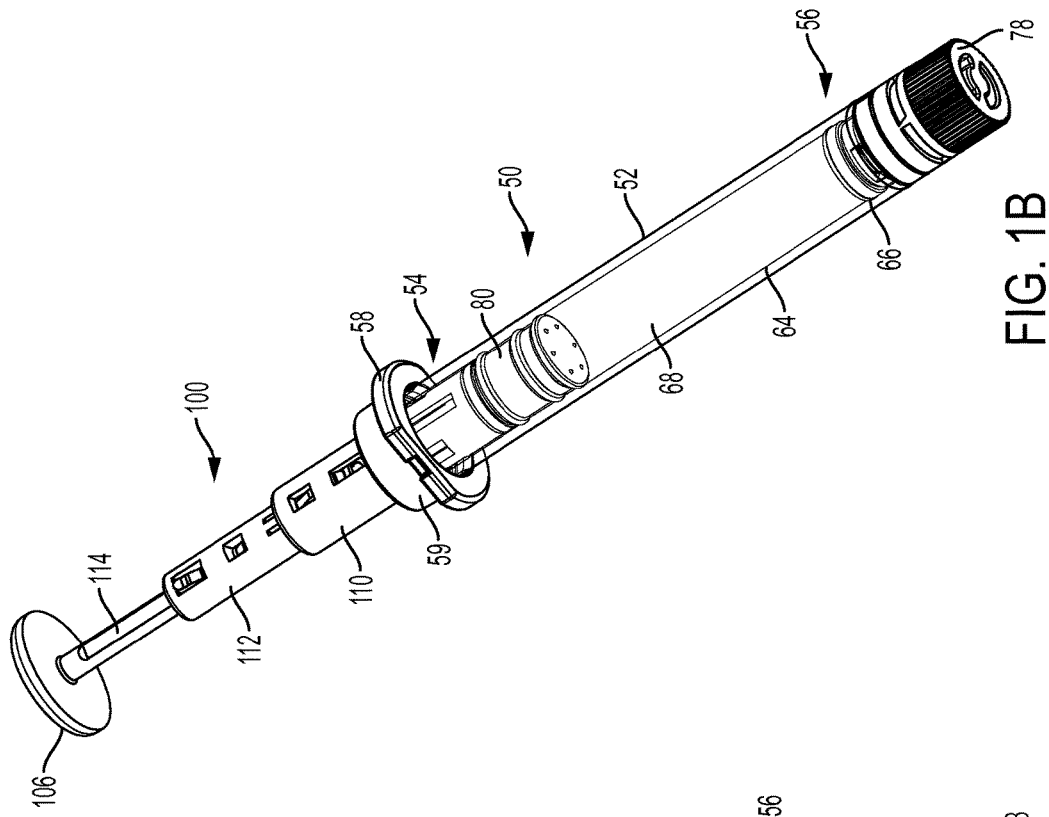
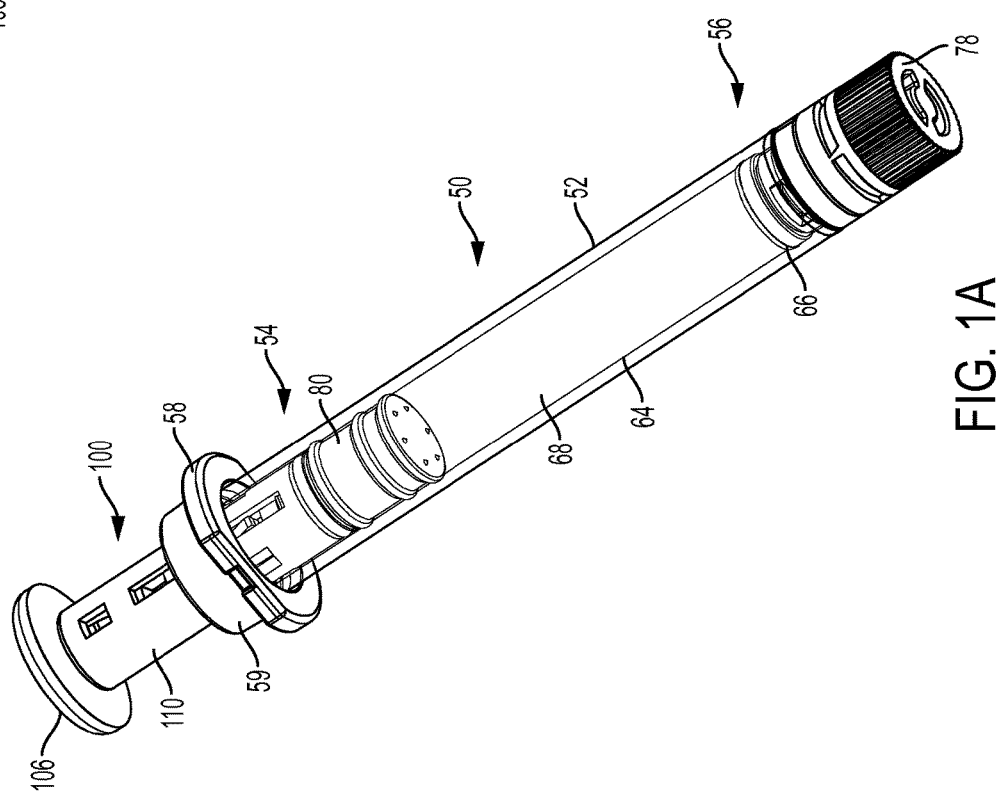

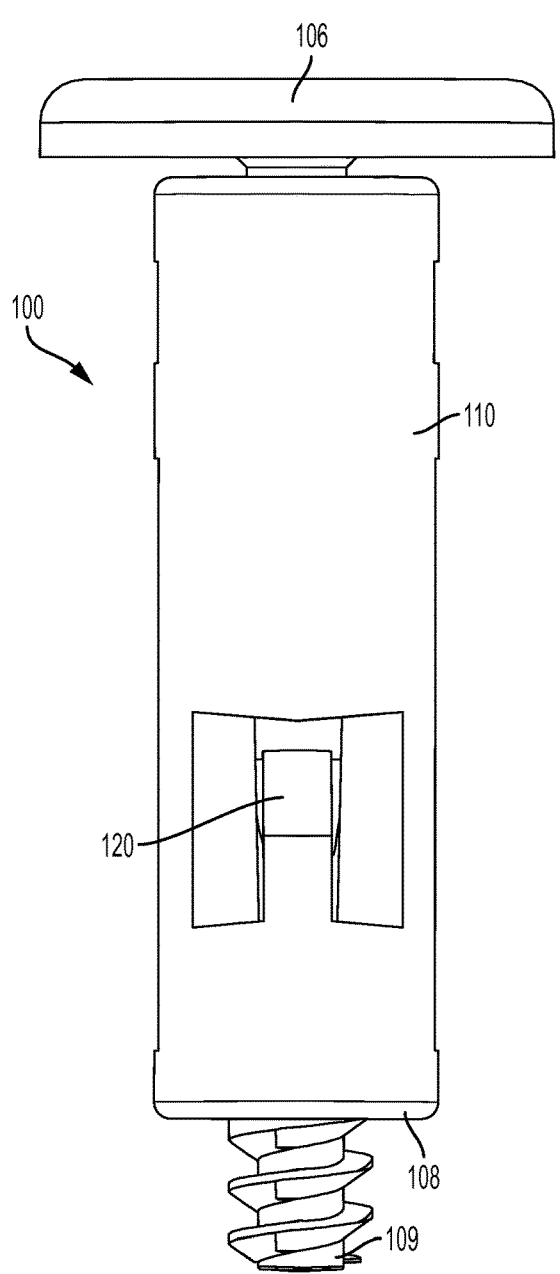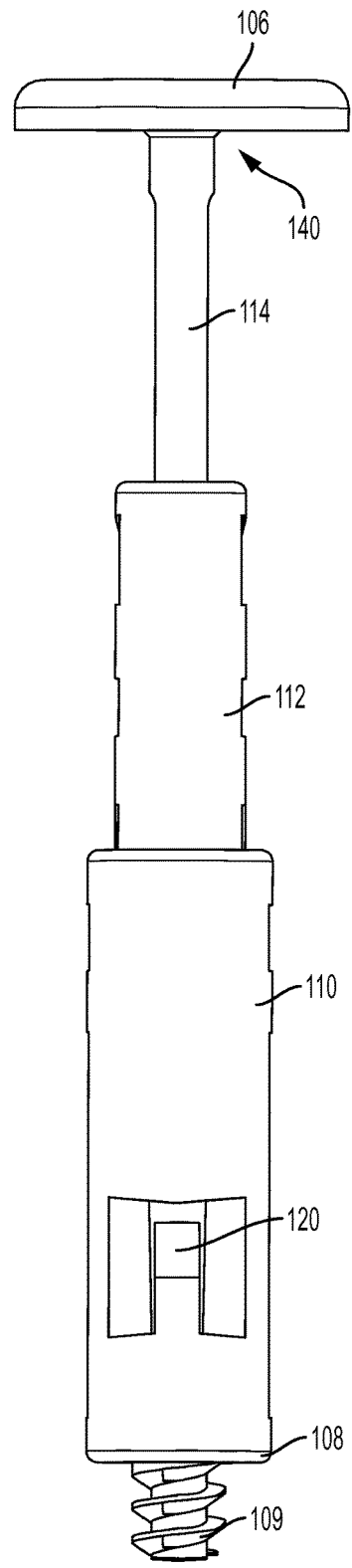
FIG. 4A
FIG. 4B

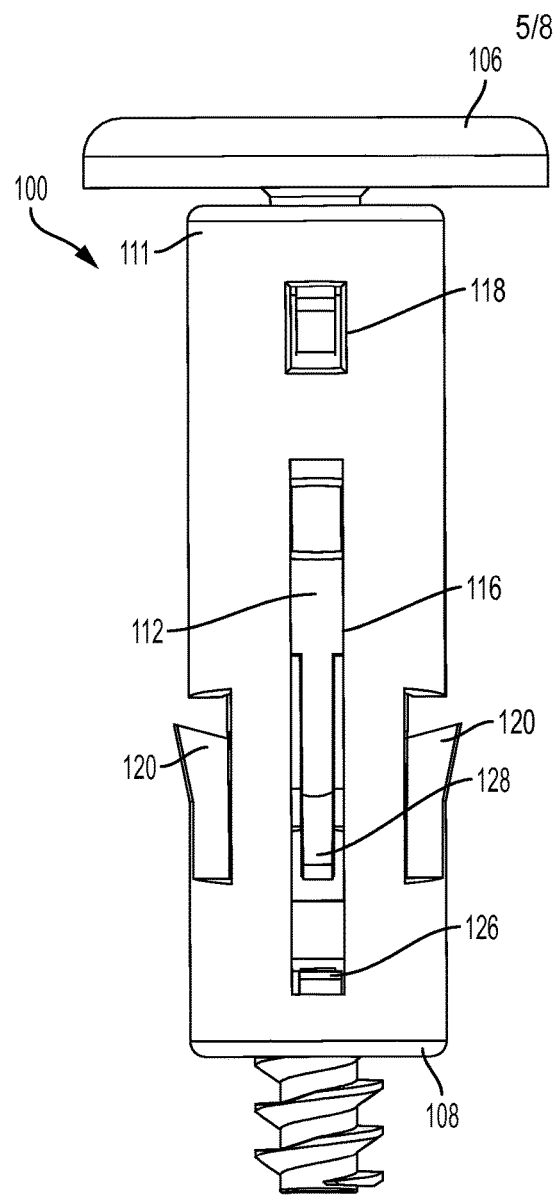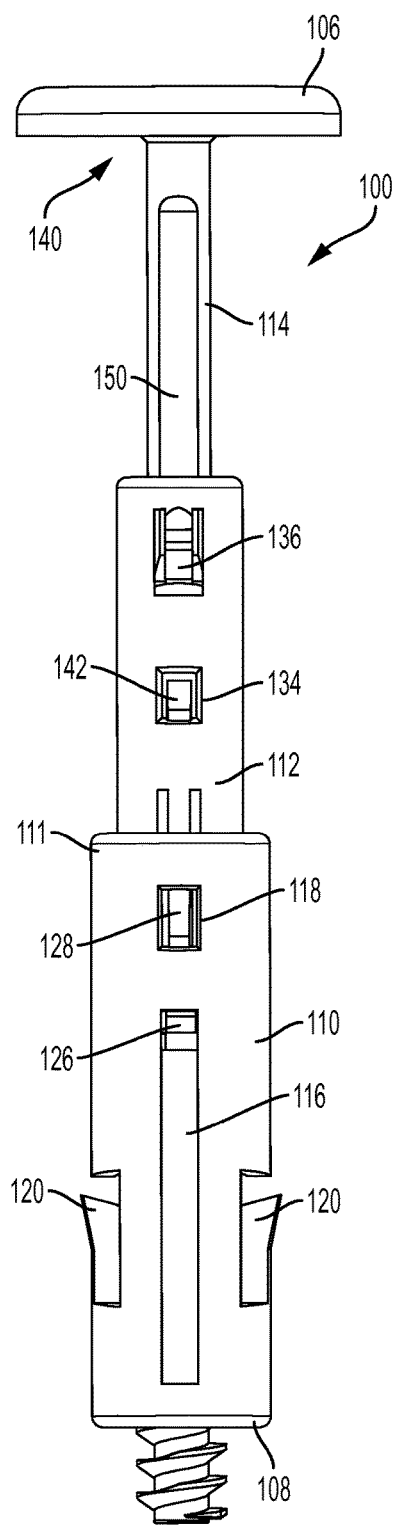
FIG. 5A
FIG. 5B

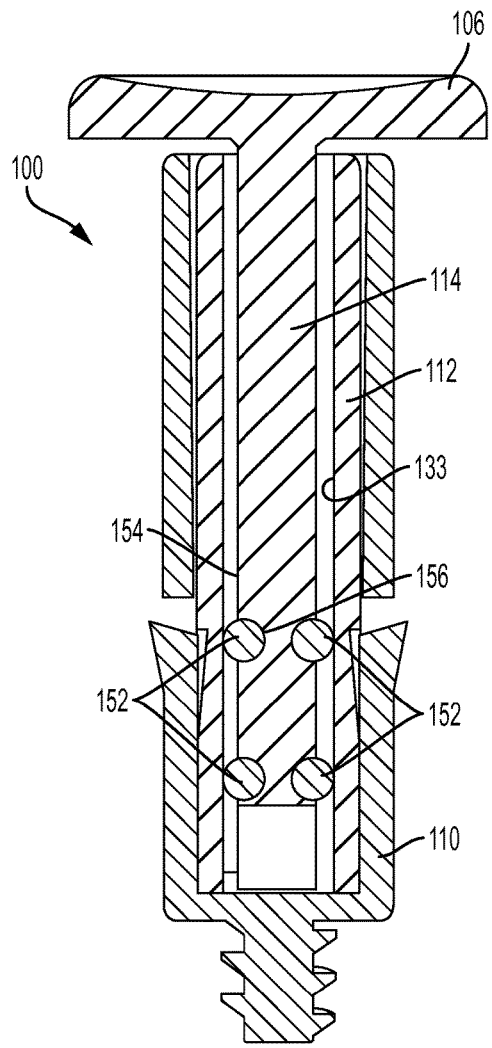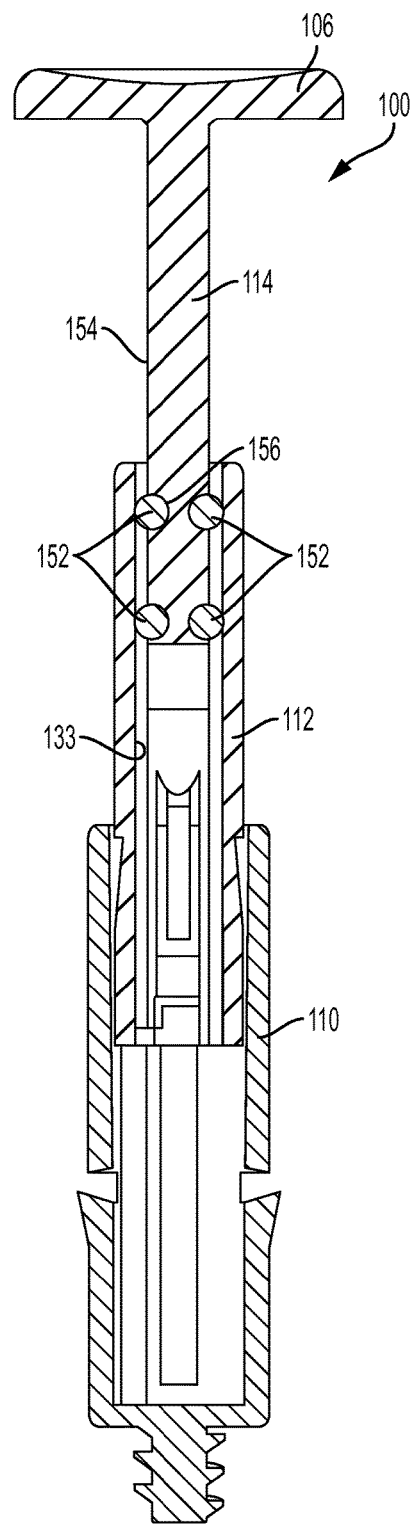
FIG. 7A
FIG. 7B

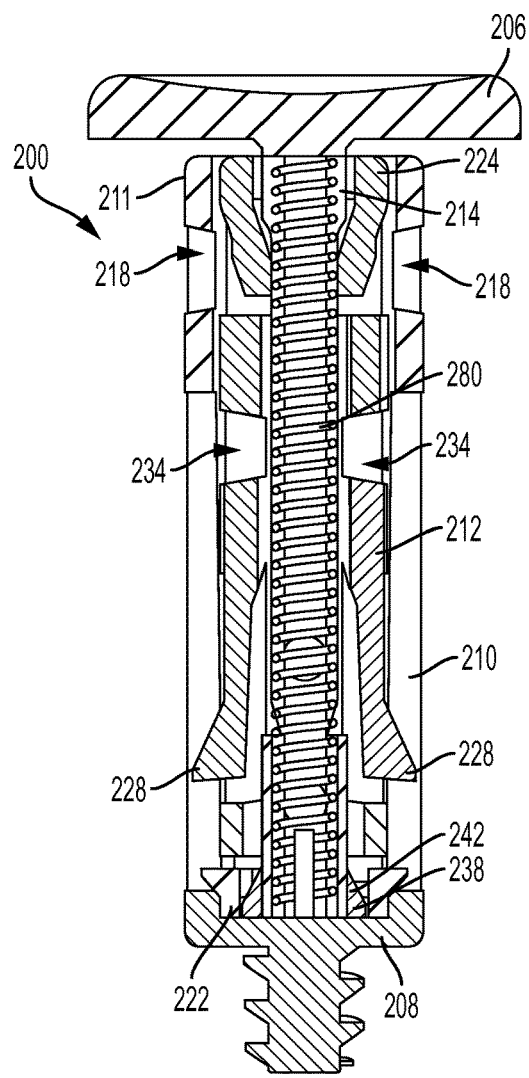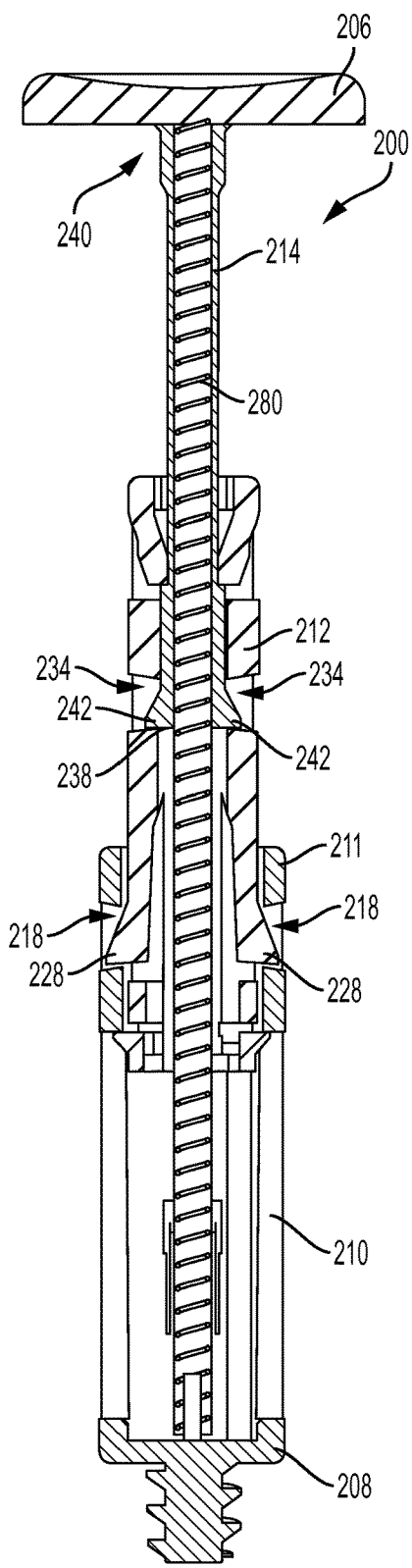
FIG. 8A
FIG. 8B

EXPANDING PLUNGER RODS FOR SYRINGES

CROSS-REFERENCE TO RELATED APPLICATIONS

This patent application is a national phase application of International Patent Application No. PCT/US2015/014255, filed Feb. 3, 2015, which claims the benefit of U.S. Provisional Patent Application No. 61/935,081, filed Feb. 3, 2014, both of which are incorporated by reference herein in their entireties for all purposes.

FIELD

THIS INVENTION relates to syringes. More particularly, this invention relates to expanding plunger rods for syringes, the syringes incorporating such plunger rods, and the use of such syringes for the delivery of fluids.

BACKGROUND

The practice of sharing syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers. Furthermore, health professionals may be exposed to used syringes which can lead to inadvertent needlestick injuries and possible exposure to infective pathogens or other contaminants.

Additionally, today's healthcare practitioner is usually provided with medical devices that are ready to use since the devices are typically sterilized during manufacture. This is particularly true of syringes that are used to administer parenteral drugs and other medical solutions.

A syringe typically includes a glass or plastic barrel having a substantially closed end and an opposite open end. The open end is sealed by a slidable piston plunger. The substantially closed end of the syringe may have a dispensing port communicating with a fitment, such as a male luer fitment, for dispensing the contents of the syringe. The syringe as manufactured may be prefilled with a liquid, part-filled with a lyophilized powder, or empty, for example. A removable end cover or cap, such as a luer cap, is placed over the fitment during manufacture so as to seal the contents within the barrel. Thus, the end cap remains sealingly in place from manufacture until the syringe is used.

The packaging of syringes may require larger dimensions than necessary or desirable, because the dimensions of such syringes for operation may be larger than the desired packaged dimensions. When packaging syringes to be shipped or stored, it is important to conserve packing space to increase the number of prefilled syringes shipped per package.

SUMMARY

The invention is, at least in part, broadly directed to a syringe having an expandable plunger rod component capable of having a smaller dimension in packaging and a larger dimension for operation.

In one aspect, the disclosure describes an expanding plunger rod for a syringe. The expanding plunger rod is configured to transition from a packaged configuration for packaging to an expanded configuration for operation. The expanding plunger rod comprises a substantially cylindrical outer sleeve having a closed-off bottom end and an open upper end. The expanding plunger rod includes an inner sleeve having a lower end and an upper end. The inner sleeve is slidably disposed coaxially within the outer sleeve. The expanding plunger rod also includes an inner rod having a lower end and an upper end. The inner rod is slidably disposed coaxially within the inner sleeve. In the packaged configuration, the inner sleeve and the inner rod are both nested within the outer sleeve. In the expanded configuration, the upper end of the inner sleeve and the lower end of the inner rod are both disposed axially above the open upper end of the outer sleeve, and the inner sleeve and inner rod are configured to lock axially in place so as to prevent transition from the expanded configuration to the packaged configuration.

The outer sleeve can include a first locking mechanism, and the inner rod can include a second locking mechanism, wherein, in the expanded configuration, the first locking mechanism and the second locking mechanism are engaged so as to prevent transition from the expanded configuration to the packaged configuration. The inner sleeve can also include locking mechanisms configured to engage with the locking mechanisms of the outer sleeve and inner rod.

The outer sleeve can include a stop mechanism configured to engage with the barrel so as to prevent the expanding plunger rod from being removed from the barrel.

In another aspect, the disclosure describes a syringe assembly configured to transition from a packaged configuration for packaging and an expanded configuration for operation. The syringe comprises a substantially cylindrical barrel having a plunger end and a connection end. The syringe includes a plunger seal disposed within the plunger end of the barrel. The syringe includes a needle seal disposed within the connection end of the barrel. The syringe includes a fluid compartment defined within the barrel between the plunger seal and the needle seal. The syringe also includes an expanding plunger rod comprising a substantially cylindrical outer sleeve having a closed-off bottom end connected to the plunger, and an open upper end. The expanding plunger rod includes an inner sleeve having a lower end and an upper end, the inner sleeve being slidably disposed coaxially within the outer sleeve. The expanding plunger rod also includes an inner rod having a lower end and an upper end, the inner rod being slidably disposed coaxially within the inner sleeve. The outer sleeve of the expanding plunger rod may be engaged with the plunger seal. The engagement may be in the form of a threaded engagement or other engagement known in the art. In the packaged configuration, the inner sleeve and the inner rod are both substantially nested within the outer sleeve. In the expanded configuration, the upper end of the inner sleeve and the lower end of the inner rod are both disposed axially above the open upper end of the outer sleeve, and the inner sleeve and inner rod are configured to lock axially in place so as to prevent transition from the expanded configuration to the packaged configuration.

In another aspect, the disclosure describes an expanding plunger rod for a syringe, the expanding plunger rod configured to transition from a packaged configuration for packaging to an expanded configuration for operation. The expanding plunger rod comprises a substantially cylindrical outer sleeve having a closed-off bottom end and an open upper end. The expanding plunger rod includes an inner sleeve having a lower end and an upper end, the inner sleeve being slidably disposed coaxially within the outer sleeve. The expanding plunger rod includes an inner rod having a lower end and an upper end, the inner rod being slidably disposed coaxially within the inner sleeve and including a top piece extending axially above the open upper end of the outer sleeve. The expanding plunger rod may include a biasing member disposed between the top piece of the inner rod and the closed-off bottom end of the outer sleeve. The biasing member biases the top piece and the bottom end axially away from one another. In the packaged configuration, the inner sleeve and the inner rod are both nested within the outer sleeve, and in the expanded configuration, the upper end of the inner sleeve and the lower end of the inner rod are both disposed axially above the open upper end of the outer sleeve, and the inner sleeve and inner rod are configured to lock axially in place so as to prevent transition from the expanded configuration to the packaged configuration. The biasing member is configured to automatically transition the expanding plunger rod from the packaged configuration to the expanded configuration.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein:

FIG. 1A shows an isometric view of a syringe having an expanding plunger rod in a packaged configuration, according to at least one embodiment of the present disclosure;

FIG. 1B shows an isometric view of the syringe of FIG. 1A in an expanded configuration;

FIG. 4A shows a front view of a manually expandable plunger rod in a packaged configuration, according to at least one embodiment of the present disclosure;

FIG. 4B shows a front view of the manually expandable plunger rod of FIG. 4A in an expanded configuration;

FIG. 5A shows a side view of the manually expandable plunger rod of FIG. 4A in the packaged configuration;

FIG. 5B shows a side view of the manually expandable plunger rod of FIG. 4A in the expanded configuration;

FIG. 7A shows a cross-sectional side view of the manually expandable plunger rod of FIG. 4A in the packaged configuration;

FIG. 7B shows a cross-sectional side view of the manually expandable plunger rod of FIG. 4A in the expanded configuration;

FIG. 8A shows a cross-sectional front view of an automatically expandable plunger rod in a packaged configuration, according to at least one embodiment of the present disclosure; and FIG. 8B shows a cross-sectional front view of the automatically expandable plunger rod of FIG. 8A in an expanded configuration.

DETAILED DESCRIPTION

Figure 2A:
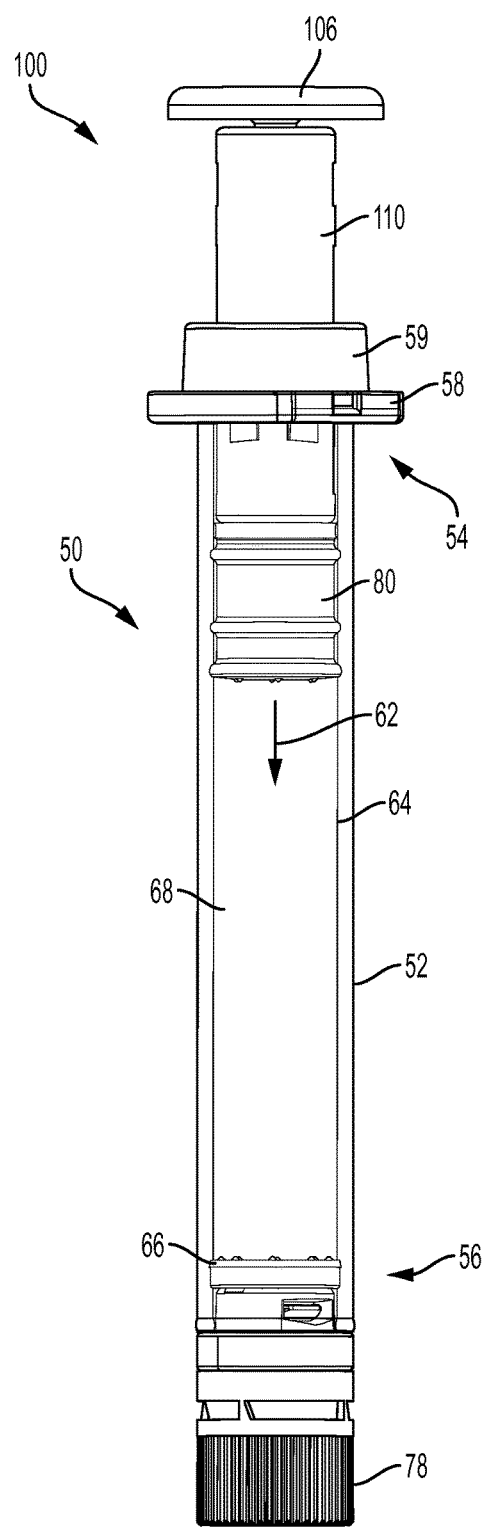
FIG. 2A shows a front view of the syringe of FIG. 1A in the packaged configuration.

The embodiments of the present invention provide expanding plunger rods which enable smaller packaging footprints (i.e., dimensions) while maintaining the usability necessary of plunger rods for syringes. Because the plunger rods of the present invention are expandable from a first position to a second or subsequent final position, they are initially capable of being assembled, packaged, transported, and stored in smaller packages, but are capable of expanding when desired for use for drug delivery. The plunger rods of the present invention are capable of being integrated and utilized within syringes for drug delivery.

Referring to FIGS. 1A and 1B, an embodiment of a syringe assembly 50 having an expanding plunger rod 100, according to at least one embodiment of the present invention, is shown. FIG. 1A shows the syringe 50 and expanding plunger rod 100 in the packaging, i.e., non-expanded, configuration, and FIG. 1B shows the syringe and expanding plunger rod in the expanded configuration. Such a syringe comprises a barrel 52 having plunger end 54 and connection end 56. The barrel 52 is substantially cylindrical in shape and is preferably formed of glass. At the plunger end 54 of the barrel 52 is located a collar 58 having a release ring 59. The collar 58 may be mounted, glued, fitted or integrally formed with the barrel 52. In embodiments where barrel 52 is formed of glass, the collar 58 is glued or otherwise adhered to the barrel. In alternative embodiments where the barrel 52 is formed of plastic or other moldable material, the collar 58 may be formed integrally with the barrel (e.g., by molding). At the connection end 56 of the barrel 52 is mounted a barrel tip adapter 60 (e.g., luer connection adapter) (see FIGS. 3A and 3B) and a tip cap 78. The syringe 50 further comprises a plunger seal 80 mounted thereto. The barrel 52 further comprises an inside wall 64 which, together with a needle seal 66 and the plunger seal 80 defines a fluid compartment 68 inside the barrel 52. In some embodiments, the needle seal 66 is mounted or located at least partly within the barrel 52 and/or a mounting member 70 (see FIGS. 3A and 3B). Accordingly, the needle seal 66 may be a component of a needle assembly, in at least one embodiment, for mounting to a barrel 52. The resulting syringes of the present disclosure which are configured to incorporate the expanding plunger rods 100 have the capability of integration into standard fill-finish filling and processing systems currently utilized by drug fillers and pharmaceutical companies, the ability to connect or engage with a range of needle assemblies and needle-less access devices ("NLADs") such as intravenous lines, the ability to prevent or minimize clogging or breakage of the connection between the syringe (or components thereof) and needle assemblies or NLADs, and the configurability of the syringes to provide drug delivery to a variety of target locations including subcutaneous and intramuscular.

Figure 2B:
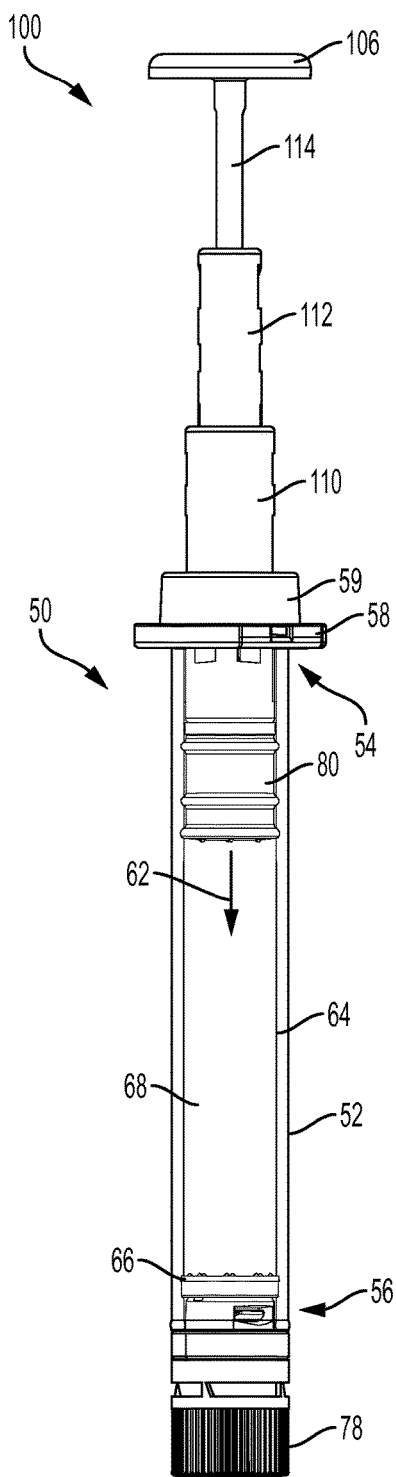
FIG. 2B shows front view of the syringe of FIG. 1A in the expanded configuration.

Referring now to FIGS. 2A and 2B, in use the plunger seal 80 is movable axially into the fluid compartment 68 in the direction of the solid arrow 62 to facilitate delivery of fluid contents of the syringe 50. In some embodiments, the fluid compartment 68 is prefilled with fluid contents to be delivered by the syringe 50. In this context, by "prefilled" is meant that the syringe 50 is provided to the user filled with deliverable fluid contents without the need for the user to fill the barrel 52 with the fluid contents.

Figure 3A:
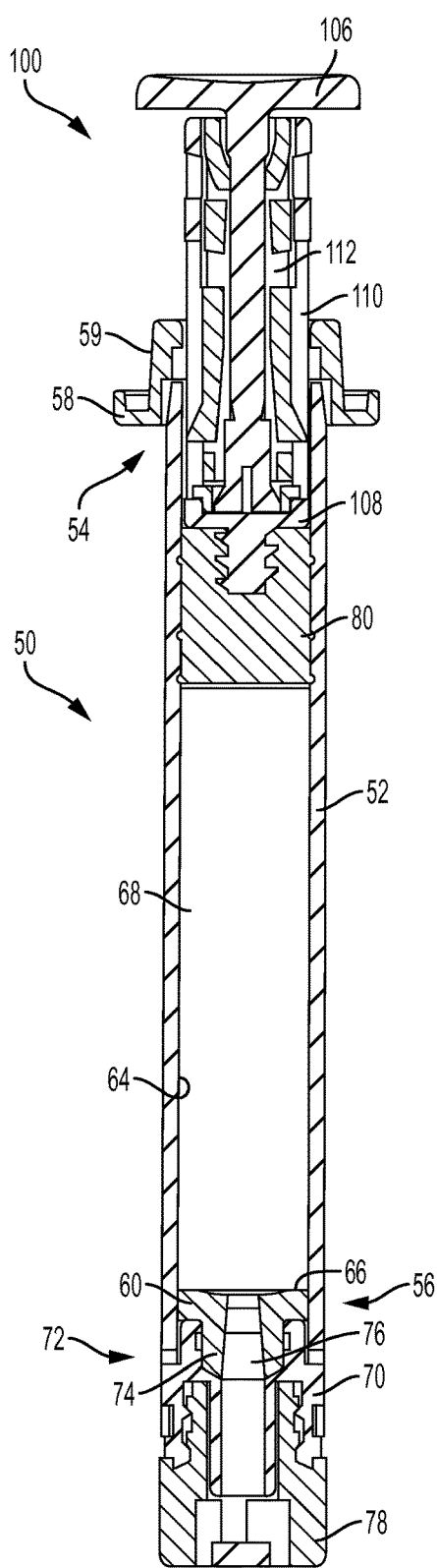
FIG. 3A shows a cross-sectional front view of the syringe of FIG. 1A in the packaged configuration.
Figure 3B:
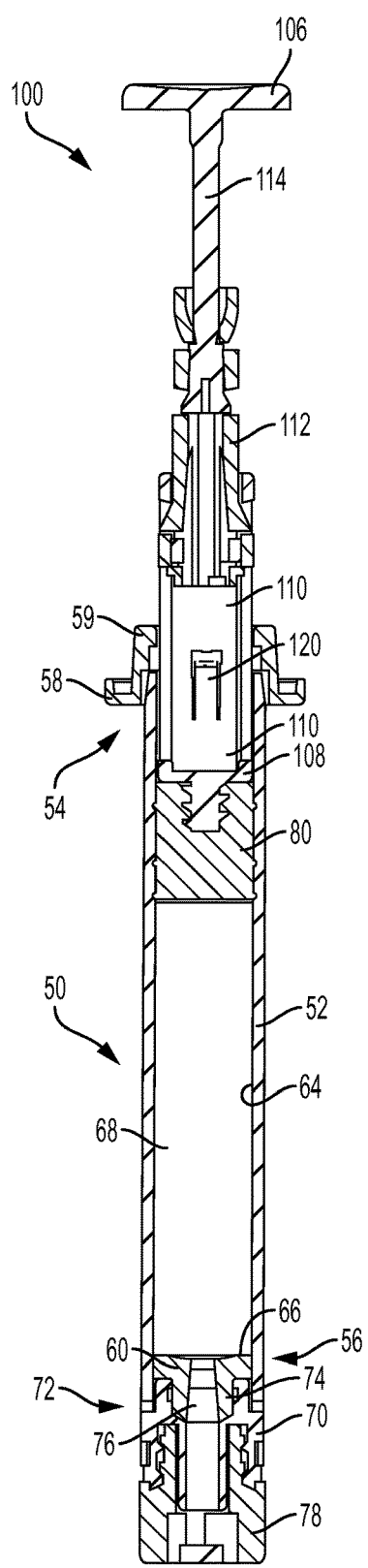
FIG. 3B shows a cross-sectional front view of the syringe of FIG. 1A in the expanded configuration.

As shown in FIGS. 3A and 3B, an adapter 60 and a mount 70 utilize a connection 72, such as a luer connection having a tapered/conical aspect and/or a screw-threaded mating configuration. When utilizing both a luer and a screw-threaded configuration, this connection may be akin to or known as a luer-lock connection. The connection adapter 60 is typically glued or otherwise firmly affixed inside the connection end 56 of the barrel 52. The adapter 60 can have a male luer fitment 74 which extends distally from the connection end 56 of the barrel 52. The male luer fitment 74 is generally tubular and is formed with a center bore 76 or central fluid passageway extending from the fluid compartment 68 within the barrel 52 to the forward tip of the male luer fitment 74. The outside surface of the male luer fitment is tapered along the extending length to provide a surface sealingly mateable with the inner tapered surface of a female luer connector. For example, the female luer connector may be in the hub of a sharp needle assembly or as part of a fluid line, such as an intravenous fluid line, connection (not illustrated). The tapered male luer fitment 74 establishes a seat for and seals with the female luer hub. Notably, the center bore 76 or central fluid passageway may be dimensioned to meet the necessary or desired requirements of the particular fluid and/or delivery mechanism. In the embodiment shown in FIGS. 2A, 2B, 3A, and 3B, a tip cap 78 is mounted to the connection end 56 of the barrel 52. In other embodiments, a needle assembly or replaceable needle assembly can be mounted or removably mounted to the adapter 60 or mount 70.

FIGS. 3A and 3B show cross-sectional front views of the syringe 50 with a manually expandable plunger rod 100 in the packaged configuration (FIG. 3A) and the expanded configuration (FIG. 3B), according to at least one embodiment of the present invention. The relatively short length of the expanding plunger rod 100 in the packaged configuration may be utilized to optimize package size, but allow for normal use upon removal from packaging and expansion into the expanded configuration. The plunger rod 100 may be configured to connect to the plunger seal 80 which, together, are slidable within a the fluid chamber 68 of a syringe barrel 52 to push or deliver a drug dose delivery to a patient. The components of the expanding plunger rod 100 are nested into one another and configured to slidably expand and lock into place with respect to one another to reach the fully expanded dimension. In some embodiments, in the expanded configuration, the expanding plunger rod 100 is wider at the interface between the plunger rod and the barrel 52 than at the top end adjacent a top piece 106. Such a configuration helps limit wobbling and radial movement of the expanding plunger rod 100 in the expanded configuration and as the plunger rod is pushed into the barrel 52. The plunger rods 100 may be expanded with or without a tip cap, needle assembly, NLAD, or other mount connected to the mounting member at the connection end 56 of the barrel 52.

In one embodiment, the expanding plunger rod 100 comprises one or more nested sleeves configured to slide upon or within each other from the packaged configuration to the expanded configuration, and to lock in place upon reaching the expanded configuration. FIGS. 4A and 4B show front views of the expanding plunger rod 100 in the packaged configuration (FIG. 4A) and the expanded configuration (FIG. 4B). The expanding plunger rod 100 includes an outer sleeve 110, an inner sleeve 112, and an inner rod 114 all configured to nest within one another in the packaged configuration. In the packaged configuration, shown in FIG. 4A, the expanding plunger rod 100 has a relatively short length compared to the length of the plunger rod in the expanded configuration shown in FIG. 4B. In some embodiments, the outer sleeve 110 has a larger diameter than the inner sleeve 112, which has a larger diameter than the inner rod 114.

The outer sleeve 110 can have a closed-off bottom end 108 that can engage with the plunger seal 80 of the syringe 50 via a threaded portion 109. The inner rod 114 can have a top piece 106 disposed at an upper end 140 of the inner rod opposite the outer sleeve 110 and the inner sleeve 112. A user can pull on the top piece 106 to move the expanding plunger rod 100 from the packaged configuration to the expanded configuration. Top piece 106 may be an integrally formed portion of inner rod 106 or, alternatively, may be a separate component attached thereto. The outer sleeve 110 can have pull-back lockout tabs 120 that may be utilized to prevent pull-out of the expanding plunger rod 100 from the plunger end 54 of the barrel 52. When installed in a barrel, such as in FIGS. 3A and 3B, the lockout tabs 120 can engage with the releasing ring 59 (or collar 58 thereof) to prevent excess axial movement of the expanding plunger rod with respect to the barrel 52.

FIGS. 5A and 5B show side views of the expanding plunger rod 100 in the packaging (FIG. 5A) and expanded (FIG. 5B) configurations. As seen from the side, the outer sleeve 110 can include a pair of pull-back lockout tabs 120, each opposite one another. The pull-back lockout tabs 120 extend radially outside the circumference of the remainder of the outer sleeve 110 so as to engage with the releasing ring 59.

The expanding plunger rod 100 may further include one or more expanding guide mechanisms, stop mechanisms, and locking mechanisms that help guide the expansion of the plunger rod, prevent the expanding plunger rod from returning to the packaged configuration after being moved into the expanded configuration, and help prevent removal of the plunger rod from the barrel 52. In some embodiments, the lockout aspects work by snapping into orifices in the outer and inner sleeves 110, 112. The various guide and locking mechanisms are best seen with general reference to FIGS. 5A, 5B, 6A, and 6B.

Figure 6A:
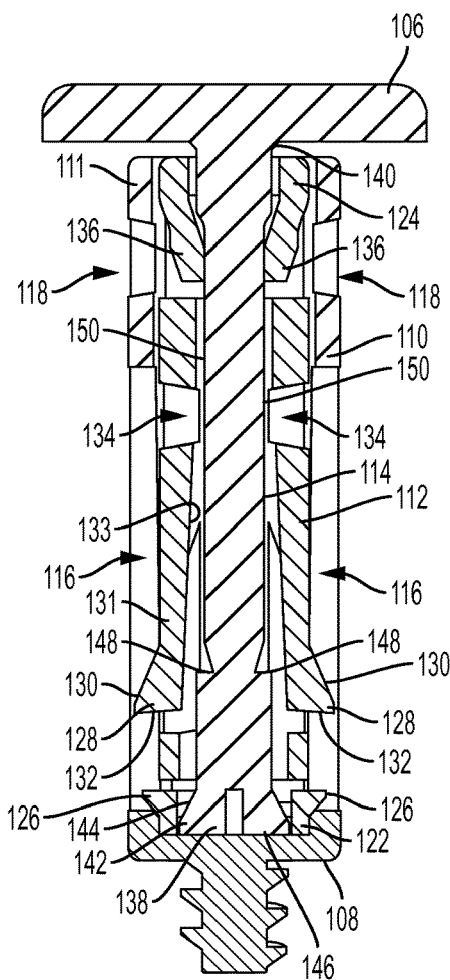
FIG. 6A shows a cross-sectional front view of the manually expandable plunger rod of FIG. 4A in the packaged configuration.
Figure 6B:
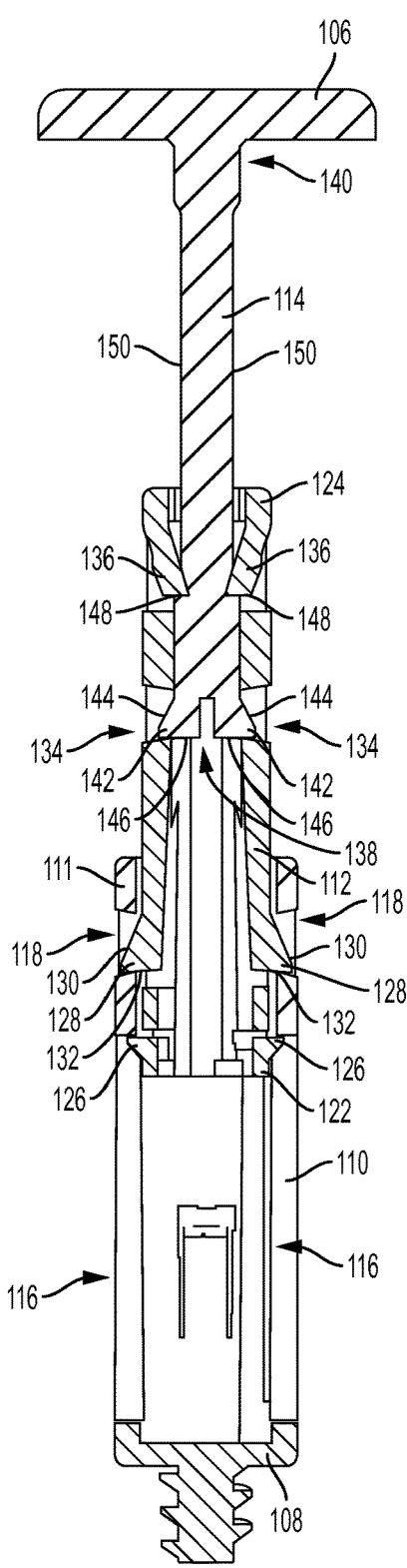
FIG. 6B shows a cross-sectional front view of the manually expandable plunger rod of FIG. 4A in the expanded configuration.

FIGS. 5A and 5B show side views of the expanding plunger rod 100 in the packaging (FIG. 5A) and expanded (FIG. 5B) configurations, while FIGS. 6A and 6B show cross-sectional front views of the expanding plunger rod 100 in the packaged configuration (FIG. 6A) and the expanded configuration (FIG. 6B). The outer sleeve 110 includes a pair of outer guide slots 116 formed on either side of the outer sleeve. As seen in FIGS. 5A and 5B, the outer guide slots 116 run longitudinally along a relatively large portion of the outer sleeve 110 between the bottom end 108 and an open upper end 111. The outer sleeve 110 also includes a pair of outer lock orifices 118 formed into either side of the outer sleeve. The outer lock orifices 118 are disposed between the outer guide slots 116 and the upper end 111 of the outer sleeve, and are longitudinally aligned with the outer guide slots. In other embodiments, the outer lock orifices are not aligned with the outer guide slots.

The inner sleeve 112 is configured to travel axially within the outer sleeve 110 and has a lower end 122 and an upper end 124. When in the packaged configuration, the lower end 122 can rest against the bottom end 108 of the outer sleeve 110. The lower end 122 of the inner sleeve 112 includes a pair of inner sleeve stops 126 disposed on either side of the inner sleeve that extend radially outward at least partially through the outer guide slots 116 of the outer sleeve 110. When the expanding plunger rod 100 is expanded, the inner sleeve stops 126 ride upward within the outer guide slots 116 as the inner sleeve 112 moves upward with respect to the outer sleeve 110. Upward movement of the inner sleeve 112 with respect to the outer sleeve 110 is halted when the inner sleeve stops 126 abut the top ends of the outer guide slots 116, as shown in FIGS. 5B and 6B.

The inner sleeve 112 also includes a pair of inner sleeve locks 128 disposed on either side of the inner sleeve. In the packaged configuration shown in FIGS. 5A and 6A, the inner sleeve locks 128 extend radially outward from the inner sleeve 112 and into the outer guide slots 116. The inner sleeve locks 128 each have a ramped upper portion 130 and a substantially flat lower portion 132. As the inner sleeve 112 moves upwards with respect to the outer sleeve 110 when the expanding plunger rod 100 expands, the inner sleeve locks 128 ride upward through the outer guide slots 116. As the ramped upper portions 130 encounter the upper ends of the outer guide slots 116, the ramped upper portions are forced radially inward. When the inner sleeve locks 128 reach the outer lock orifices 118 of the outer sleeve 110, the inner sleeve locks are biased radially outward into the outer lock orifices. The flat lower portions 132 of the inner sleeve locks 128 can then abut the lower ends of the outer lock orifices 118, preventing the inner sleeve 112 from moving downward with respect to the outer sleeve 110, such as is shown in FIG. 6B.

The inner sleeve 112 includes a pair of inner lock orifices 134 formed into the inner sleeve between the inner sleeve locks 128 and the upper end 124 of the inner sleeve. The inner sleeve 112 also includes a pair of stop tabs 136 disposed on either side of the inner sleeve between the inner lock orifices 134 and the upper end 124 of the inner sleeve. The stop tabs 136 are configured so as to be biased radially inward against the inner rod 114 when the expanding plunger rod 100 is in the packaged configuration, as shown in FIG. 6A.

The inner rod 114 is configured to travel axially within the inner sleeve 112 and has a lower end 138 and an upper end 140. When in the packaged configuration, the lower end 138 can rest against the bottom end 108 of the outer sleeve 110, and the top end 140 connected to the top piece 106 extends out of both the upper end 111 of the outer sleeve 110 and the upper end 124 of the inner sleeve 112. The lower end 138 of the inner rod 114 includes a pair of inner rod locks 142. The inner rod locks 142 each have a ramped upper portion 144 and a substantially flat lower portion 146. In the packaged configuration, the inner rod locks 142 fit within the lower end 122 of the inner sleeve 112. As the expanding plunger rod 100 is expanded, the inner rod 114 moves upward with respect to the inner sleeve 112. In some embodiments, the interior surface 133 of the inner sleeve 112 can have a tapered portion 131 that tapers inwardly between the inner sleeve locks 128 and the inner lock orifices 134. As the inner rod locks 142 move upward through the tapered portion 131 of the inner sleeve 112, the interior surface of the inner sleeve can press against the ramped upper portion 144, forcing the inner rod locks 142 radially inward. When the inner rod locks 142 reach the inner lock orifices 134, the inner rod locks snap into the inner orifices. Thus, in the expanded configuration, as shown in FIG. 6B, the inner rod locks 142 extend radially outward into the inner lock orifices 134, and the flat lower portions 146 of the inner rod locks 142 abut the lower end of the inner lock orifice to prevent the inner rod 114 from moving downward with respect to the inner sleeve 112.

The inner rod 114 includes a pair of inner rod stops 148 formed into either side of the inner rod between the inner rod locks 142 and the upper end 140 of the inner rod. The inner rod stops 148 are substantially flat and face generally upward toward the upper end 140 of the inner rod 114. The inner rod 114 also has two substantially flat wall portions 150 on either side of the inner rod between the inner rod stops 148 and the upper end 140 of the inner rod. In the packaged configuration shown in FIG. 6A, the stop tabs 136 of the inner sleeve 112 press radially inward against either flat wall portion 150. As the expanding plunger rod 100 is expanded and the inner rod 114 moves upward with respect to the inner sleeve 112, the stop tabs 136, which are biased inward, slide against the flat wall portion 150 until the stop tabs encounter the inner rod stops 148. In the expanded configuration, such as is shown in FIG. 6B, the stop tabs 136 abut the inner rod stops 148, preventing the inner rod 114 from being pulled further axially upward with respect to the inner sleeve 112.

In some embodiments, anti-rotation ribs may also be utilized to prevent the plunger rod components (sleeves, etc.) from rotating with respect to one another. In some embodiments, a shroud may be utilized to prevent the user from delivering or releasing drug dose before the plunger rod 100 is fully expanded. In the illustrated embodiment, the outer sleeve 110 is configured to engage the plunger seal 80 (or stopper). In an alternative embodiment, however, a sleeve other than an outer most nested sleeve (e.g., an inner most sleeve or any other sleeve) can be configured to engage a plunger seal (or stopper). It should be understood that, although the illustrated embodiments tend to show pairs of locking and guiding aspects on opposite sides of the expanding plunger rod 100, it is contemplated that more or fewer locking and guiding aspects can be used in other embodiments. Further, in some embodiments, other lockout components may be utilized to prevent the plunger from being depressed in the distal direction after use to prohibit re-use. Although shown with two expanding sleeves, it is contemplated that the expanding plunger rod may have any number of sleeves. For example, the expanding plunger rod may consist of an inner rod disposed in a single sleeve. Alternatively, the plunger rod may include three or more sleeves.

FIGS. 7A and 7B show cross-sectional side views of the expanding plunger rod 100 in the packaged configuration (FIG. 7A) and the expanded configuration (FIG. 7B). In some embodiments, the expanding plunger rod 100 includes bearings 152 disposed substantially between the interior surface 133 of the inner sleeve 112 and the inner rod 114. As the expanding plunger rod 100 expands from the packaged configuration in FIG. 7A to the expanded configuration in FIG. 7B, the bearings 152 roll along an outer surface 154 of the inner rod 114 and the interior surface 133 of the inner sleeve 112. In some embodiments, the bearing 152 can be rotatably disposed within bearing pockets 156 in the inner rod. The bearings 152 can help provide a smooth, rolling interface between the inner rod 114 and the inner sleeve 112, and can help keep the inner rod properly aligned within the inner sleeve. Recesses may be formed in the inner sleeve which may serve as tracks within which the bearings may translate during expansion of the plunger rod, thereby further controlling the motion of the bearings. Although the embodiment illustrated in FIGS. 7A and 7B include four bearings 152, it should be understood that more or fewer bearings can be used in other embodiments. It is also contemplated that, in some embodiments, additional bearings can be disposed between the outer sleeve 110 and the inner sleeve 112.

FIGS. 8A and 8B show an alternative embodiment of an expanding plunger rod of the present invention may be automatically expanding plunger rod 200. Unless otherwise noted, it should be understood that the features of automatically expanding plunger rod 200 are substantially similar to the features of the manually expanding plunger rod 100 described herein. FIGS. 8A and 8B show cross-sectional front views of an automatically expandable plunger rod 200 in the packaged configuration (FIG. 8A) and the expanded configuration (FIG. 8B), according to at least one embodiment of the present invention. The automatic expanding plunger rod 200 includes an outer sleeve 210, an inner sleeve 212, and an inner rod 214 all configured to nest within one another in the packaged configuration. The outer sleeve 210 includes a closed-off bottom end (208) and an open upper end (211). The inner sleeve 212 includes a lower end 222 and an upper end 224, and the inner rod 214 has a lower end 238 and an upper end 240. The inner rod 214 includes a top piece 206 that extends axially above the open upper end 211 of the outer sleeve 210 in the packaging configuration, as shown in FIG. 8A. The outer sleeve 210 includes a pair of outer lock orifices 218 formed on either side of the outer sleeve, and the inner sleeve 212 includes a pair of inner sleeve locks 228 disposed on either side of the inner sleeve. The inner sleeve 212 also includes a pair of inner lock orifices 234 formed on either side of the inner sleeve, and the inner rod 214 includes a pair of inner rod locks 242 disposed on either side of the inner rod. In the expanded configuration, the inner sleeve locks 228 extend radially outward into the outer lock orifices 218, and the inner rod locks 242 extend radially outward into the inner lock orifices 234 so as to prevent transition from the expanded configuration to the packaged configuration.

The user may activate the automatic expanding plunger rod 200 by, for example, pushing, twisting, pulling, or another action/combination of actions that releases a device that causes a biasing member 280, such as a spring, to expand the plunger rod 200 automatically. In the illustrated embodiment, the biasing member 280 is disposed axially within the inner rod 214, an inner sleeve 212, and the outer sleeve 210. The biasing member can be any device which can store energy in a releasable form, such as a spring (e.g., a coil spring, leaf spring etc.) elastic or the like. Although only one biasing member 280 is shown in the embodiment shown in FIGS. 8A and 8B, it is contemplated that other embodiments could use multiple biasing members to automate the expansion of the expanding plunger rod 200. In the embodiment shown in FIGS. 8A and 8B, the biasing member 280 is configured to push on the top piece 206 of a inner rod 214 and a bottom end 208 of the outer sleeve of the expanding plunger rod 200. The biasing member 280 forces the expanding plunger rod open (i.e., to expand) once automatic expansion is activated by the user. In at least one embodiment, the outer most nested sleeve 210 is configured to engage a plunger seal (or stopper). In an alternative embodiment, however, a sleeve other than the outer most nested sleeve (e.g., the inner most sleeve or any other sleeve) is configured to engage a plunger seal (or stopper).

In one embodiment, a platform may be utilized to prevent any load or force from the spring to be transferred to the plunger seal. The platform may help to limit or prevent premature drug delivery and/or drug loss. In such embodiments, the biasing member may be completely internal and the platform or tab may be removable by the user, for example, after the automatic expansion of the plunger rod has occurred and the expanding plunger rod is locked into its expanded configuration for drug dose delivery. Alternatively, the tab or platform may yield at a given point and/or may be moved, such as moved radially, to clear the path for axial plunger rod travel during drug delivery.

The embodiments of the present invention may further utilize additional components to enhance the use of the syringe. For example, the syringe may incorporate tamper-resistance aspects to prevent tampering of the syringe. These tamper-resistance aspects deter or prevent a user from, for example, removing the plunger rod and/or providing evidence of tampering to the user. These tamper-resistance aspects could be located along the plunger rod, plunger seal, and/or the barrel flange, collar, and/or release ring. These tamper-resistance aspects could be axially positioned and/or longitudinally oriented, or in a number of other known configurations. In one embodiment, the tamper-resistance aspects may be tamper tabs. These tamper-resistance aspects impact upon the barrel flange, collar, and/or release ring to prevent pulling the plunger rod out of the barrel in the proximal direction. The tamper-resistance aspects may additionally or alternatively be located on an optional stability ring or flange of the plunger rod. Optionally, the syringes of the present invention may utilize tamper-evident features. For example, the syringes and/or adapters may utilize an over-sized or specially-shaped tip cap that cannot be reinserted into the syringe after removal. Alternatively, the syringes and/or adapters may utilize tamper tabs that connect the tip cap to itself through a window in the adapter during assembly, but cannot be reassembled. As a further embodiment, the tip cap or tip cap assembly may be bonded to the barrel tip during assembly, and a broken bond could be utilized to provide visual indication of tampering.

The connection adapters of the present invention may utilize a locking aspect that is incorporated, for example, into a standard luer thread pattern. This configuration may be utilized to lock an attachment, such as a needle assembly, to the syringe via the adapter. The locking aspect and/or lock feature(s) may alternatively, or additionally, be internal to the adapter. Such locking aspects and adapters may be utilized with a proprietary connection and/or a luer connection. The figures show the attachment of the adapter to a straight barrel, such as a straight glass barrel, but this can also be utilized to attach to a tapered or formed-shape barrel. The adapter may have a ledge to facilitate easy mounting and attachment (such as by glue or adhesive) to the distal end of a barrel. An internal window ledge may be utilized for needle seal attachment, and also to prevent movement of the needle seal.

In some embodiments, the invention provides a retractable syringe kit comprising a barrel, a plunger and a plurality of replaceable needle assemblies. In one embodiment of the retractable syringe kit, the plurality of needle assemblies comprise a 0.5 inch needle, a 1.0 inch needle, and a 1.5 inch needle, though a range of needle lengths and gauges may be utilized and incorporated within the needle assemblies and kits of the present invention.

In a particular embodiment, the retractable syringe kit further comprises a vial adapter. In one particular form, the vial adapter comprises a housing having a base, an adapter cannula that extends or projects from the base and a connector that is capable of being in fluid communication with fluid contents of a vial and the barrel of said retractable syringe, the adapter housing further comprising a shroud to protect a user from inadvertent needle-stick injury by said adapter cannula, said shroud comprising one or more arms that engage a vial closure. The shroud may further comprise one or more flexion arms that allow the vial adapter to engage any of a variety of different-sized vial closures. In use, the vial adapter facilitates transfer or delivery of fluid between the vial and the syringe barrel to thereby allow fluid reconstitution of a powdered, dried, desiccated or dehydrated solid substance contained within the syringe barrel or within the vial.

In one embodiment, the invention provides a method of assembling a syringe including the step of inserting or attaching the expanding plunger rod to the proximal end of a barrel of a syringe. Optionally, a releasing ring and/or a collar may be present on the proximal end of the barrel for engagement with the plunger rod. The method of assembly may further include the step of connecting the expanding plunger rod to a plunger seal. Preferably, the method includes the step of removing a plug from a mounting member of the barrel prior to removably mounting the replaceable mount to the barrel. In one embodiment, the method includes the step of screw-threadedly mounting a mount of a needle assembly or NLAD to a mounting member of the barrel.

In developing syringes with needle safety mechanisms, relatively complicated component assemblies have been utilized which add substantially to the complexity and cost of manufacture. Additionally, existing configurations may not adequately address challenges related to: patient and user safety needs, user ease-of-operation, and drug filler or pharmaceutical company operational systems, among others. In developing a selectable needle safety syringe having a retraction plunger, the inventors of the present invention have addressed these challenges and others without comprising the manufacturability, stability, and durability of the devices.

Additionally, in providing a means for selectable attachment of varying needle assemblies, the present invention provides configurations that are capable of being adapted for a broad range of drug barrel (i.e., primary container) types. Existing devices possess relatively complicated luer assemblies have been devised which often are adapted for a particular syringe barrel shape or configuration and cannot be readily mounted to a syringe barrel having a different shape or configuration. This is particularly a problem with glass syringe barrels which are generally in short supply, many of which glass barrels do not have a desired shape or configuration for mounting a luer assembly. Alternatively, the syringes may be manufactured with a pre-formed luer assembly. However this adds substantial complexity and cost to the process for manufacture of such syringes.

Each of the embodiments described herein may be used alone or in combination with one or more other embodiments in a syringe. Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

We claim:

1. An expanding plunger rod for a syringe, the expanding plunger rod configured to transition from a packaged configuration for packaging to an expanded configuration for operation, the expanding plunger rod comprising:
   a substantially cylindrical outer sleeve having a closed-off bottom end and an open upper end;
   an inner sleeve having a lower end and an upper end, the inner sleeve being slidably disposed coaxially within the outer sleeve; and
   an inner rod having a lower end and an upper end, the inner rod being slidably disposed coaxially within the inner sleeve;
   wherein, in the packaged configuration, the inner rod is nested within the inner sleeve, and the inner sleeve is nested within the outer sleeve, the lower end of the inner rod resting against the closed-off bottom end of the outer sleeve, the outer sleeve including a pull-back lockout tab configured to prevent removal of the outer sleeve from a barrel of the syringe; and
   wherein, in the expanded configuration, the upper end of the inner sleeve and the lower end of the inner rod are disposed substantially axially above the open upper end of outer sleeve, and the inner rod is configured to lock axially in place so as to prevent transition from the expanded configuration to the packaged configuration.

2. The expanding plunger rod of claim 1, wherein the closed-off bottom end of the outer sleeve is configured to connect to a plunger seal, the outer sleeve and the plunger seal being slidable within a fluid compartment of the syringe.

3. The expanding plunger rod of claim 1, wherein the outer sleeve includes a first stop mechanism, the inner sleeve includes a second stop mechanism and a third stop mechanism, and the inner rod includes a fourth stop mechanism, wherein, in the expanded configuration, the first stop mechanism is engaged with the second stop mechanism and the third stop mechanism is engaged with the fourth stop mechanism so as to prevent further axial travel of the inner sleeve and the inner rod away from the outer sleeve.

4. The expanding plunger rod of claim 1, wherein the outer sleeve includes a first locking mechanism, the inner sleeve includes a second locking mechanism and a third locking mechanism, and the inner rod includes a fourth locking mechanism, and wherein, in the expanded configuration, the first locking mechanism is engaged with the second locking mechanism and the third locking mechanism is engaged with the fourth locking mechanism so as to prevent transition from the expanded configuration to the packaged configuration.

5. A syringe assembly configured to transition from a packaged configuration for packaging to an expanded configuration for operation, the syringe assembly comprising:
   a substantially cylindrical barrel having a plunger end and a connection end;
   a plunger seal disposed within the plunger end of the barrel;
   a needle seal disposed within the connection end of the barrel;
   a fluid compartment defined within the barrel between the plunger seal and the needle seal; and
   an expanding plunger rod comprising:
   a substantially cylindrical outer sleeve having a closed-off bottom end connected to the plunger seal, and an open upper end,
   an inner sleeve having a lower end and an upper end, the inner sleeve being slidably disposed coaxially within the outer sleeve, and
   an inner rod having a lower end and an upper end, the inner rod being slidably disposed coaxially within the inner sleeve;
   wherein, in the packaged configuration, the inner sleeve and the inner rod are both nested within the outer sleeve, the lower end of the inner rod resting against the closed-off bottom end of the outer sleeve, the outer sleeve including a stop mechanism configured to engage with the barrel so as to prevent the expanding plunger rod from being removed from the barrel; and wherein, in the expanded configuration, the upper end of the inner sleeve and the lower end of the inner rod are both disposed axially above the open upper end of the outer sleeve, and the inner sleeve and inner rod are configured to lock axially in place so as to prevent transition from the expanded configuration to the packaged configuration.

6. The syringe assembly of claim 5, wherein the outer sleeve includes a first locking mechanism, the inner sleeve includes a second locking mechanism and a third locking mechanism, and the inner rod includes a fourth locking mechanism, and wherein, in the expanded configuration, the first locking mechanism is engaged with the second locking mechanism and the third locking mechanism is engaged with the fourth locking mechanism so as to prevent transition from the expanded configuration to the packaged configuration.

7. The syringe assembly of claim 6, wherein the first locking mechanism is an outer lock orifice formed into a side of the outer sleeve and the second locking mechanism is an inner sleeve lock disposed on a side of the inner sleeve, wherein, in the expanded configuration, the inner sleeve lock extends radially outward into the outer lock orifice.

8. The syringe assembly of claim 7, wherein the third locking mechanism is an inner lock orifice formed into a side of the inner sleeve, and the fourth locking mechanism is an inner rod lock disposed on a side of the inner rod, wherein, in the expanded configuration, the inner rod lock extends radially outward into the inner lock orifice.

9. The syringe assembly of claim 5, wherein the outer sleeve and the plunger seal are slidable within the fluid compartment of the syringe assembly to expel fluid out of the fluid compartment.

10. The syringe assembly of claim 5, wherein the barrel further comprises a collar disposed at the plunger end of the barrel, the stop mechanism of the outer sleeve being configured to engage with the collar to so as to prevent the expanding plunger rod from being removed from the barrel.

11. The syringe assembly of claim 5, wherein the outer sleeve includes a first stop mechanism, the inner sleeve includes a second stop mechanism and a third stop mechanism, and the inner rod includes a fourth stop mechanism, wherein, in the expanded configuration, the first stop mechanism is engaged with the second stop mechanism and the third stop mechanism is engaged with the fourth stop mechanism so as to prevent transition further axial travel of the inner sleeve and the inner rod away from the outer sleeve.

* * * * *